United States Patent [19]

Shoesmith

[11] Plant 4,829

[45] Mar. 9, 1982

[54] CHRYSANTHEMUM NAMED ROCKET

[75] Inventor: Leonard H. Shoesmith, Westfield-Woking, England

[73] Assignee: Pan-American Plant Company, West Chicago, Ill.

[21] Appl. No.: 170,006

[22] Filed: Jul. 18, 1980

[51] Int. Cl.[3] ..... A01H 5/00

[52] U.S. Cl. ..... Plt./76

[58] Field of Search ..... Plt./76; Plt./80-81

*Primary Examiner*—Robert E. Bagwill

*Attorney, Agent, or Firm*—Rummler and Snow

[57] ABSTRACT

A new and unique chrysanthemum for Fall gardens (early response) or for year-around four inch pot production (four weeks response), distinguished by its many vibrant pink daisy-like flowers, having bright yellow centers, borne on strong, upright stems; the plant having a vigorous, upright growth and profuse blooming habit whereby the plant forms a mound of color when garden bloomed in the Fall.

4 Drawing Figures

BACKGROUND OF THE NEW PLANT

My new chrysanthemum cultivar originated as a seedling of unknown parentage growing among breeding stock maintained at West Chicago, Ill., where I discovered this new plant. The vibrant pink coloration of the daisy-like flowers of this plant prompted me to select it for propagation and test, which was done under my direction at West Chicago, Ill. Asexual propagation of this new plant by means of cuttings through several successive generations has shown that its novel characteristics hold true from generation to generation and appear to be firmly fixed. Propagation by cuttings for the commercial market is now being done at West Chicago, Ill., and at Cortez, Fla.

DESCRIPTION OF THE DRAWINGS

My new chrysanthemum cultivar is illustrated by the accompanying drawings, of which sheet 1 is a full color photographic rendition showing a garden plant in full bloom; sheet 2 is a photographic close-up face view of flowers of the new plant which has been hand-painted to show the true colors of the blooms according to specifications; and sheets 3 and 4, respectively, are prints of machine copies of the front and back-sides of typical leaves of this new variety.

DESCRIPTION OF THE NEW PLANT

The following is a detailed description of my new chrysanthemum cultivar based upon observations of plants grown at West Chicago, Ill., made in the Fall of 1979, the color designations being according to The R.H.S. Colour Chart published by The Royal Horticultural Society of London, England.

THE PLANT

Origin: Seedling.
Parentage: Unknown.
Classification:
- *Botanic.*—*Chrysanthemum morifolium.*
- *Commercial.*—Chrysanthemum for either garden or greenhouse pot culture.

Form: Herbacious bush of generally round shape.
Height: 50 to 75 cm.
Growth: Vigorous, strong and upright.
Branching character: Caespitose.

Foliage:
- *Quantity.*—Abundant.
- *Leaf size.*—Length — about 3.5 to 5 cm. Width — about 3 to 4 cm.
- *Leaf shape.*—Ovate with cleft margins.
- *Texture.*—Leathery.
- *Venation.*—Pinnate.
- *Color.*—Upper side — 137A. Under side — 137C.
- *Petioles.*—Length: about 10 to 20 mm.

THE BUD

Form: Globular.
Size: Variable in both diameter and length.
Opening rate: Normal.
Color of florets:
- *When phyllaries first divide.*—61A.
- *When florets begin to unfurl.*—61A.

Phyllaries:
- *Number.*—Approximately 12.
- *Shape.*—Lanceolate.
- *Color.*—139D.

Peduncle:
- *Length.*—Variable.
- *Character.*—Rigid and erect.
- *Surface aspect.*—Canescent.
- *Color.*—139D.

THE FLOWER

Flowering capability: Recommended for garden flowering in early Fall as well as for year-around four inch pot production with photoperiod control.
Response:
- *In garden.*—Early.
- *Greenhouse pot.*—Seven week.

Natural flowering season: Early Fall.
Blooms:
- *Habit.*—Plant blooms profusely.
- *Flower type.*—Daisy.
- *Size.*—Small. Diameter — about 20 to 35 mm. Depth — about 8 to 12 mm.
- *Borne.*—Cymose.
- *Shape.*—When bloom first opens — cup-shaped. When bloom matures — flat.

Petalage:
- *Phyllaries.*—Approximately twelve in number.
- *Florets.*—Ray florets — approximately twenty-five. Disc florets — numerous. Arrangement:

Imbricated. Form: Elliptic with entire margins and rounded apex. Texture: Soft. Appearance: Satiny. Color: Ray florets: Body — 67A. Base — 62D. Reverse side — 67D. Disc florets — 14A.

Peduncle: Strong and upright.

*Length.*—Variable.

*Color.*—139D.

Discoloration after full bloom: Ray florets fade to 67B.

Persistence: The florets hang on and dry.

Fragrance: Typical chrysanthemum.

Lasting quality:

*On plant.*—Four weeks.

*As cut flower.*—Not recommended.

REPRODUCTIVE ORGANS

Stamens:

*Number.*—Many in syngenesious arrangement.

*Anthers.*—Size: Insignificant. Color: Yellow.

*Filaments.*—Length: Insignificant. Color: Yellow.

*Pollen.*—Color:Yellow.

Pistils:

*Number.*—One for each floret.

*Styles.*—Length: Insignificant. Color: Yellow.

*Stigmas.*—Color: Yellow.

Ovaries: Inferior bicarpellate.

This new chrysanthemum cultivar is unique in its capability for Fall garden use, as well as for year-around photoperiod controlled four inch pot plant production, with a seven week response. This new plant is further distinguished by its profuse production of its daisy-like flowers which have vibrant pink ray florets surrounding a central disc of bright yellow color. The flowers are borne on strong upright stems and the vigorous growth of the plant forms a mound of color when garden bloomed in the Fall.

I claim:

1. A new and distinct chrysanthemum cultivar substantially as herein shown and described, particularly characterized in uniqueness as a garden variety for early Fall blooming, as well as for use as a plant for year-around four inch pot production under photoperiod control, and by its profuse production of pink daisy-like flowers having bright yellow centers.

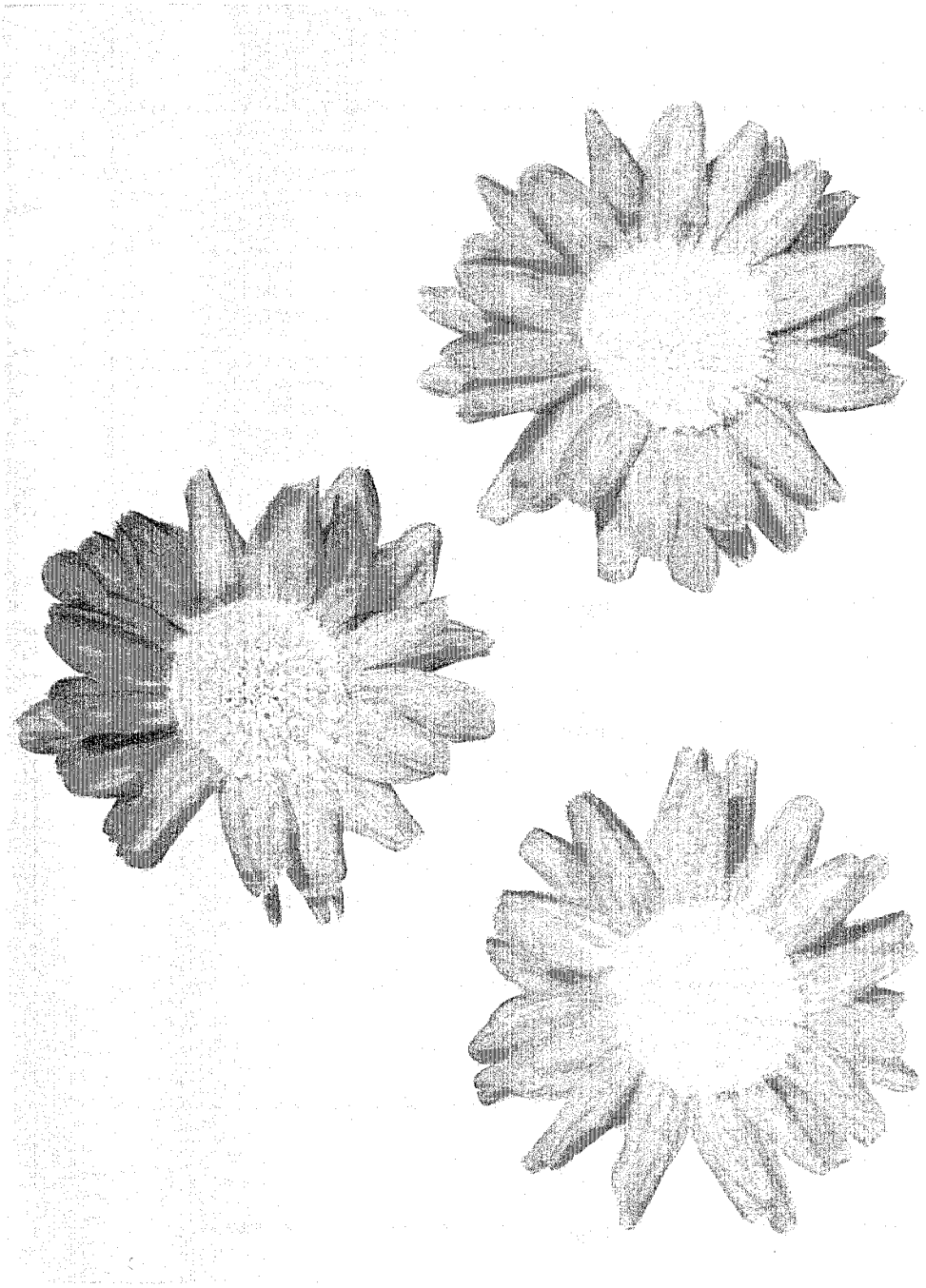

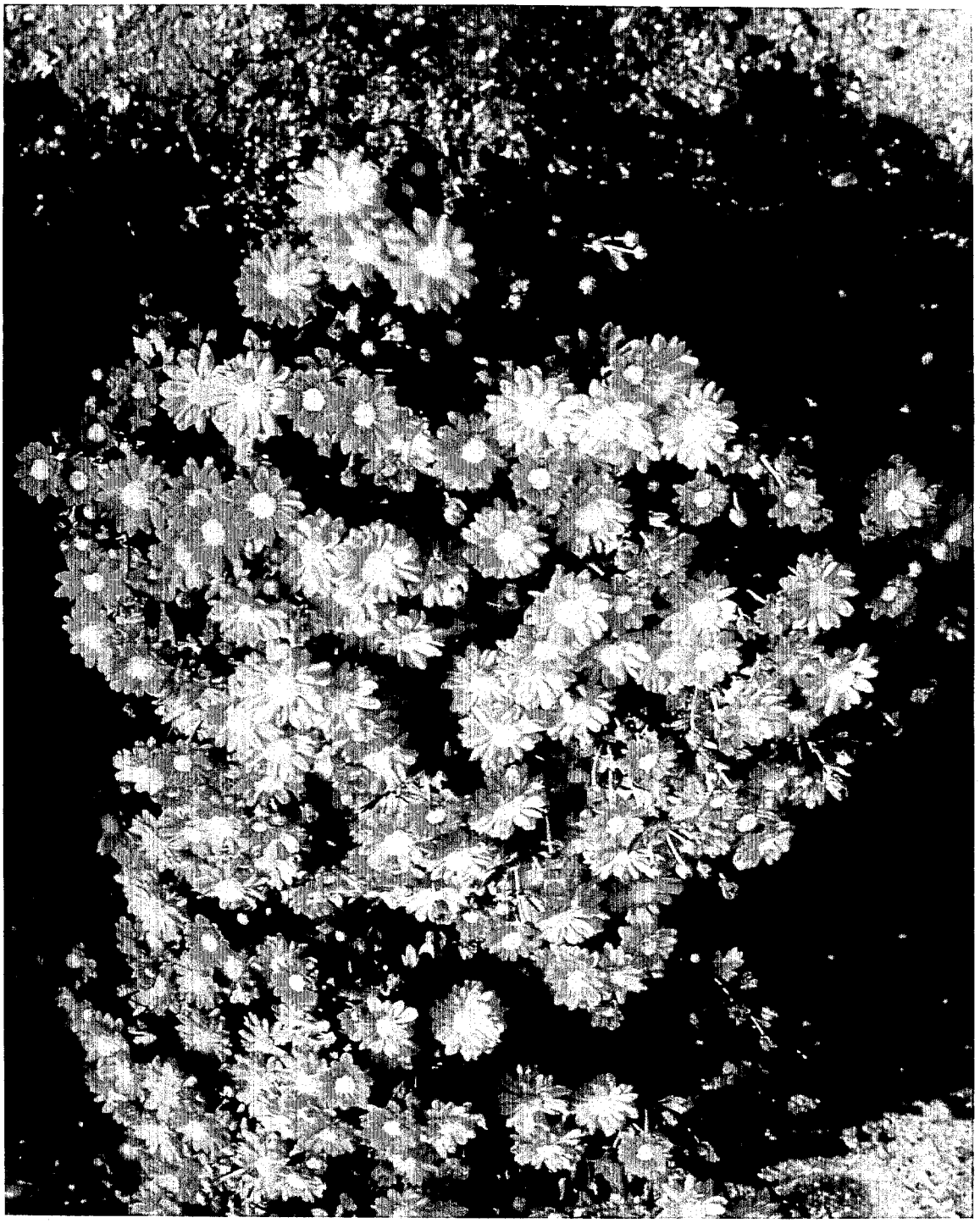

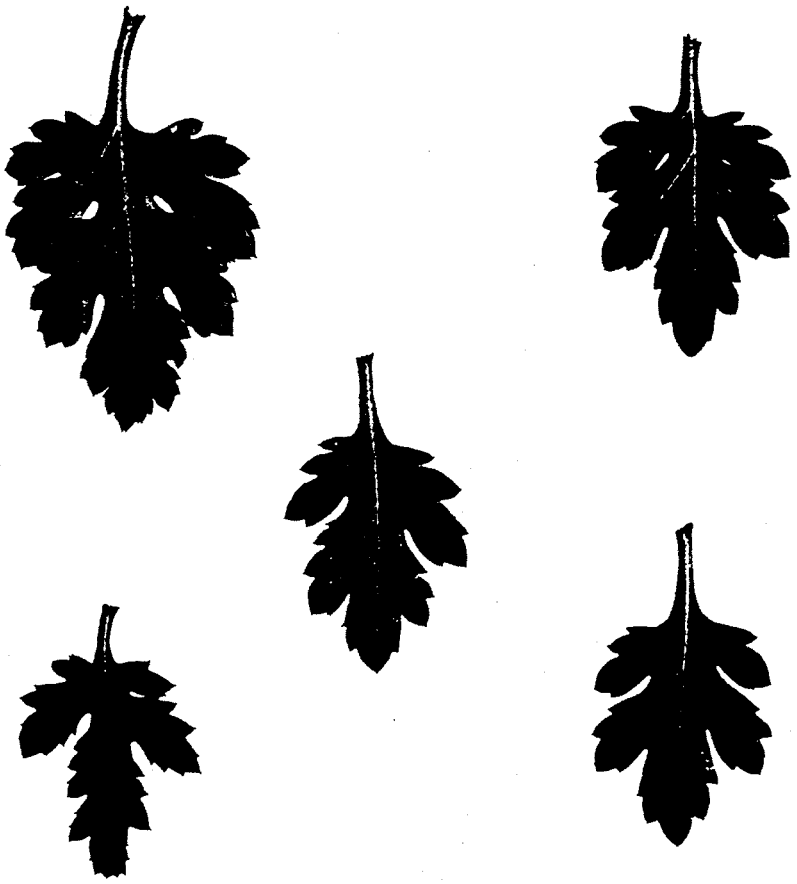

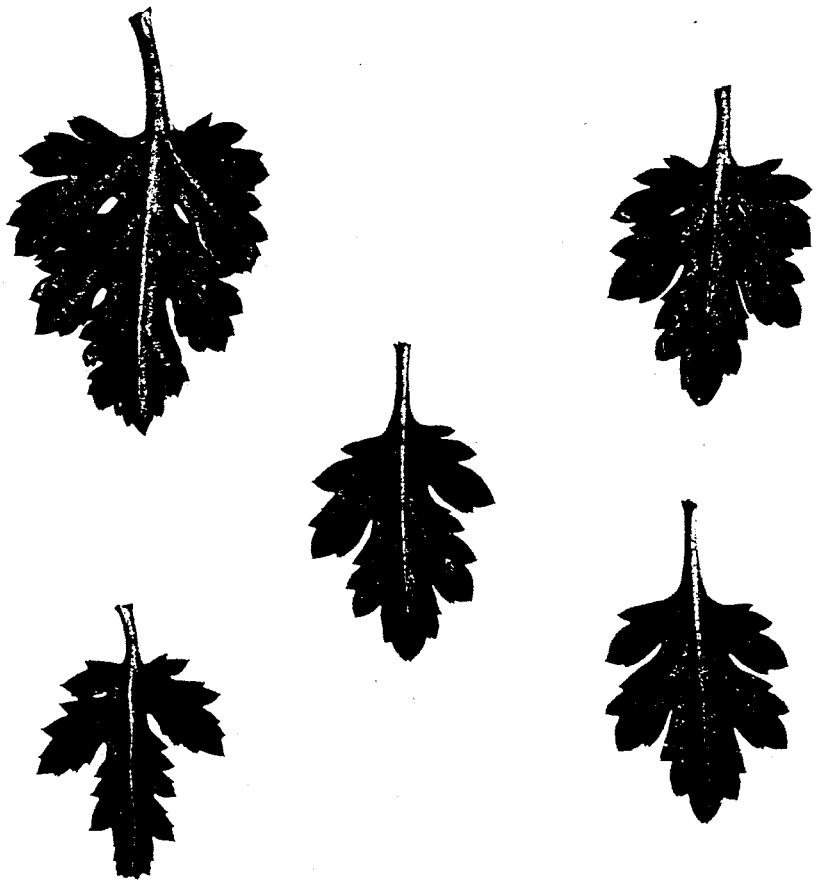

* * * * *